US006687377B2

(12) United States Patent  
Voix et al.

(10) Patent No.: US 6,687,377 B2
(45) Date of Patent: Feb. 3, 2004

(54) METHOD AND APPARATUS FOR DETERMINING IN SITU THE ACOUSTIC SEAL PROVIDED BY AN IN-EAR DEVICE

(75) Inventors: Jeremie Voix, Montreal (CA); Frederic Laville, Montreal (CA)

(73) Assignee: Sonomax Hearing Healthcare Inc., Montreal (CA)

(*) Notice: Subject to any disclaimer, the term of this patent is extended or adjusted under 35 U.S.C. 154(b) by 538 days.

(21) Appl. No.: 09/739,962

(22) Filed: Dec. 20, 2000

(65) Prior Publication Data

US 2002/0076057 A1 Jun. 20, 2002

(51) Int. Cl.[7] .......................... H04R 29/00; A61B 5/00
(52) U.S. Cl. ........................ 381/60; 600/559; 73/585
(58) Field of Search ................... 381/60, 57, 58, 381/328, 329, 71.6; 181/129, 130, 134, 135; 73/585; 600/559; 128/864

(56) References Cited

U.S. PATENT DOCUMENTS

| | | | |
|---|---|---|---|
| 4,412,096 A | * 10/1983 | Edgerton et al. | 381/60 |
| 4,615,007 A | 9/1986 | King et al. | 600/559 |
| 4,809,708 A | * 3/1989 | Geisler et al. | 600/559 |
| 5,044,373 A | 9/1991 | Northeved et al. | 600/559 |
| 5,317,273 A | 5/1994 | Hanson et al. | 324/616 |
| 5,577,511 A | 11/1996 | Killion | 600/559 |
| 5,757,930 A | 5/1998 | Seidmann et al. | 381/60 |
| 5,923,764 A | 7/1999 | Shennib | 381/60 |
| 5,970,795 A | 10/1999 | Seidmann et al. | 73/585 |
| 5,991,417 A | * 11/1999 | Topholm | 381/60 |
| 6,118,877 A | * 9/2000 | Lindemann et al. | 381/60 |

FOREIGN PATENT DOCUMENTS

WO      WO 94/22372      * 10/1994      ............... 381/60

* cited by examiner

*Primary Examiner*—Xu Mei (57) ABSTRACT

The present invention provides an apparatus for determining in situ the acoustic seal provided by an in-ear device of a hearing protection/aid nature inserted into the ear canal of an individual. The in-ear device having a sound bore with an environment opening and an ear opening outside and inside the ear canal respectively, the environment opening is adapted to be removably engaged by a remote device such as a sound measurement device, a filter device, an amplifier device, a plug device and the like. The apparatus includes a sound measurement device having a probe microphone and a reference microphone isolated from each other and connected to a data processing unit having a control box and a speaker, both connected to a computer unit. Both microphones are adapted for measuring sound pressure levels inside said ear canal and outside in close proximity of said in-ear device respectively, the sound pressure levels corresponding to a known noise signal created by the speaker. The data processing unit being adapted for recording and processing the sound pressure levels read by both microphones corresponding to said known noise signal to provide a corresponding calculated value of a sound pressure level difference provided by the in-ear device. Used in conjunction with an expandable in-ear device, the apparatus monitors the acoustic seal in real time during the occlusion process of the in-ear device and determines when to stop the process. The present invention also refers to a corresponding method for determining in situ the acoustic seal provided by an in-ear device.

20 Claims, 3 Drawing Sheets

METHOD AND APPARATUS FOR DETERMINING IN SITU THE ACOUSTIC SEAL PROVIDED BY AN IN-EAR DEVICE

FIELD OF THE INVENTION

The present invention relates to in-ear devices and more particularly to a method and an apparatus for determining in situ the acoustic seal provided by in-ear devices, such as hearing aid devices (HADs), ear protection devices (HPDs) and the like.

BACKGROUND OF THE INVENTION

The noisy environment in our industrial society is a health hazard to numerous workers as well as to people engaged in recreational activities generating loud noises.

Users often wear earplugs when operating light machinery such as chainsaws or heavy machinery such as paper industry, printing industry, aircraft industry machines, when participating in sporting activities such as shooting, and when attending various spectator events such as automobile races, truck pulls, and rock concerts, and the like.

Prior art mentions "universal fit" type earplugs, these plugs are often termed "universal fit" because they are intended to adapt to the contours of any person's ear canal to provide hearing protection. To install the "universal fit" earplug, the wearer must first compress and/or form the plug by kneading, wadding or rolling it up and then position the plug in his or her ear canal. In the case of the foam earplug, the plug must be inserted before it expands.

Those "universal fit" earplugs are difficult for many individuals to insert properly. If the plug is formed by the user incorrectly as it is inserted in the ear canal, wrinkles and voids may develop that allow sound leakage to the user's eardrum, thereby reducing the protective effectiveness of the plugs to the wearer. Also, some of the plugs typically are larger than people may need because it has been designed to fit ear canals that are larger than average in hopes of accommodating a wide range of users. Finally, some users find "universal fit" earplugs to be uncomfortable and touching the foam earplug, to roll it, with dirty fingers can lead to infection of the external and middle ear.

Custom-molded earplugs can be an attractive alternative to "universal fit" earplugs and have advantages in their comfort, more reliable fit and lower long-term costs due to longer usable life. Also, custom-molded earplugs may offer certain hygiene advantages in dirty environments since the user does not have to compress or form them with their fingers prior to insertion.

Casting an earplug in situ using a self-curing resin is not an ideal method for creating a custom-molded earplug. A doctor or a trained technician will be required to make the mold since the mould's manufacture requires a highly viscous resin or putty to be deposited deep in the patient's ear. The objective when taking the ear mold is to obtain an impression, which follows all inner contours of the ear canal and which, has no voids or creases due to the trapped air pockets. Packing the resin in the ear canal to meet this objective can be very painful to the patient. After the resin is added to the ear, it may be necessary to manually apply some pressure from outside the ear to assure that the resin hardens within the canal. The patient must sit motionless, without jaw movement, for several minutes until the mold solidifies.

Besides severe pain being caused to many patients, casting an earplug in situ also suffers from the common problem of voids being formed therein which reduce the effectiveness of the final earplug produced.

Semi-custom-molded expandable earplug may also offer the same advantages. The person to be fitted with this earplug is first fitted with a pre-shaped earplug having the approximate shape of the ear canal of the individual. Preferably the pre-shaped device is made available in different basic sizes to obtain the closest size corresponding to the individual. The size chosen should allow a small gap to permit an optimum expansion accomplished with an injected settable compound material. It is very important in that case to be precise in the quantity of injected compound because a little excess can create an inflating pressure level that can be very painful to the patient and, at the same time, an earplug cannot provide an effective acoustic seal with less inflating pressure. It is very difficult or even impossible to attain that optimum expansion without determining in situ the acoustic seal provided by an earplug.

All the above specifically refer to earplugs but it is to be understood that it is similarly applicable to any in-ear device, the latter referring to either earplug device (or hearing protection device (HPD)) or hearing aid device (HAD) for which an attenuation level or an amplification performance level is seek respectively.

U.S. Pat. No. 5,757,930 issued to Seidmann on May 26, 1998 and U.S. Pat. No. 5,790,795 issued to Seidmann on Oct. 26, 1999 disclose an apparatus being adapted only for in-ear sound level measurement without any comparison with an environmental sound. U.S. Pat. No. 5,577,511 issued to Killion on Nov. 26, 1996 discloses the occluding object and method for measuring its occlusion from existing surrounding noise without wide band measurement from any control sound sources. This measuring device cannot effectively be used to determine an accurate sound level difference provided by the object.

Furthermore U.S. Pat. No. 5,044,373 issued to Northeved on Sep. 3, 1991 relates to the method and apparatus for measuring of sound pressure levels in the auditory canal of a person in connection with the fitting of said apparatus. Authors used the reference microphone located far from in-ear device and moreover, this apparatus may be inserted only besides traditional in-ear device. As a result, this invention misrepresented a real sound level difference provided by the in-ear device inserted into an ear canal of an individual and is especially unsuitable for measuring sound level difference provided by earplugs as opposed to amplification of hearing aid devices. According to this invention the best thing would be if its probe could be placed at a distance approx. 1 mm from the eardrum. However, it is difficult to do this while making sure that the probe does not touch the eardrum, the reason being that the length and shape of the auditory canal differ from person to person.

Additionally, there is no objective way of measuring an insertion loss (IL) value provided by an in-ear device. The IL estimation described in all standards (ANSI, ISO, CSA, etc.) is subjectively determined by the individual wearing the in-ear device, as better described herebelow.

OBJECTS OF THE INVENTION

An object of the present invention is to provide a method and an apparatus for determining in situ the acoustic seal provided by an in-ear device for either of a hearing protection/aid nature that obviates the above-mentioned disadvantages.

Another object of the present invention is to provide a method and an apparatus for determining in situ the acoustic seal provided by an in-ear device that ensures a perfect fit and a good acoustic seal of the device easily obtainable with a good comfort for the potential user.

A further object of the present invention is to provide a method and an apparatus for determining in situ the acoustic seal provided by an in-ear device that allows for an effective protection against noise in the case of hearing protectors and an elimination of the noise feedbacks in the case of hearing communication/aid devices.

Still another object of the present invention is to provide a method and an apparatus for determining in situ the acoustic seal provided by an in-ear device that allows for a monitoring of the ear canal occlusion during the settable compound injection session of expandable in-ear devices.

Still further object of the present invention is to provide a method and an apparatus for determining in situ the acoustic seal provided by an in-ear device that allows for an effective performance in the sound insulation, attenuation, communication, measurement and the like of in-ear devices.

Yet another object of the present invention is to provide a method and an apparatus for determining in situ the acoustic seal provided by an in-ear device that allows for an objective estimation of the insertion loss provided by in-ear devices, and an estimation value of any standard parameters that could be derived therefrom.

Other objects of the present invention will become apparent from a careful reading of the detailed description provided herein, with appropriate reference to the accompanying drawings.

SUMMARY OF THE INVENTION

According to an aspect of the present invention, there is provided an apparatus for determining in situ an acoustic seal provided by an in-ear device inserted into an ear canal of an individual, said in-ear device having a sound bore with an environment opening and an ear opening outside and inside said ear canal respectively, said environment opening being adapted to be removably engaged by a remote device such as a sound measurement device, a filter device, an amplifier device, a plug device and the like, said apparatus comprises a sound measurement device being said remote device and having a probe microphone and reference microphone isolated from each other and connected to a data processing unit having a control box and a reference sound source, both connected to a computer unit, said probe and reference microphones being adapted for measuring a sound pressure level inside said ear canal of said individual and a sound pressure level from said environment in close proximity of said in-ear device respectively, said sound pressure levels corresponding to a known noise signal created by said reference sound source at an inlet to the individual's ear in a close proximity of said in-ear device, said data processing unit being adapted for recording and processing said sound pressure levels read by both said probe and reference microphones corresponding to said known noise signal to provide a corresponding calculated value of a sound level difference provided by said in-ear device.

Preferably, the in-ear device is expandable and further has an injection channel with an opened end outside said ear canal and a closed end inside said in-ear device adapted to receive a settable compound material allowing for said in-ear device to properly assume said ear canal of said individual, said apparatus being adapted for continuously monitoring said calculated value of said sound level difference while said compound material being simultaneously slowly injected into said expandable in-ear device via said injection channel, said data processing unit being adapted for advising to stop injecting said compound material into said expandable in-ear device upon obtaining a calculated value of a sound pressure level difference of said in-ear device achieving first occurring of being either substantially equal to a predetermined sound pressure level difference or a substantially time stable sound level difference conditions.

Preferably, either the predetermined sound pressure level difference or the time stable sound level difference is determined over a pre-selected frequency range.

Preferably, the computer unit includes a display member for displaying said calculated value of said sound level difference provided by respective of said in-ear devices.

Alternatively, the apparatus further comprises a second measurement device adapted to engage an environment opening of a sound bore of a second in-ear device inserted into a second ear canal of said individual, said second measurement device being simultaneously connected to said control box of said data processing unit for the same to simultaneously provide a second corresponding calculated value of a sound level difference provided by said second in-ear device.

Preferably, the control box is adapted for filtering and sequentially sending said sound pressure levels read by said probe and reference microphones of said in-ear device to said computer unit.

Preferably, the control box being adapted for filtering said sound pressure levels read by said probe and reference microphones of both of said in-ear devices and having a multiplexer for sequentially sending the same to said computer unit.

Alternatively, the in-ear device has a second sound bore with an environment opening and an ear opening outside and inside said ear canal respectively, said environment opening of said second sound bore being adapted to be removably engaged by a second remote device, said second remote device being either an amplifier device or filter device adapted for a pre-selected frequency window, said second remote device engaging said environment opening of said second sound bore during measuring said sound pressure levels by said probe and reference microphones.

Preferably, the computer unit contains pre-determined correction factors and a transfer coefficient, said apparatus determining an estimated insertion loss value provided by said in-ear device from said calculated value of said sound level difference and said pre-determined correction factors and transfer coefficient.

According to another aspect of the present invention, there is provided a method for determining in-situ the acoustic seal provided by an in-ear device inserted into an ear canal of an individual, said in-ear device having a sound bore with an environment opening and an ear opening outside and inside said ear canal respectively, said environment opening being adapted to be removably engaged by a remote device such as a sound measurement device, a filter device, an amplifier device, a plug device and the like, said method comprises the steps of:

a) providing said sound measurement device having a probe microphone and a reference microphone isolated from each other and a data processing unit having a control box and a reference sound source, both connected to a computer unit, b) turning on said data processing unit;

c) connecting said measurement device to said data processing unit;

d) testing connection of said measurement device to said data processing unit by measuring a known noise signal from said reference sound source with said probe and reference microphones;

e) engaging said measurement device into said environment opening of said sound bore, said probe and reference microphones for measuring a sound pressure level inside said ear canal of said individual and a sound pressure level from said environment in close proximity of said in-ear device respectively;

f) sending a known noise signal from said reference sound source;

g) recording sound pressure levels read by both said probe and reference microphones corresponding to said known noise source signal;

h) processing said measured sound pressure levels;

i) obtaining a calculated value of a sound level difference provided by said in-ear device;

j) turning off said data processing unit;

k) disconnecting said measurement device from said data processing unit; and l) disengaging said measurement device from said in-ear device.

Preferably, the method further comprises, after step b), the step of:

b1) performing calibration of said data processing unit to check proper connection of said control box to said computer unit.

Preferably, the in-ear device is expandable and further has an injection channel with an opened end outside said ear canal adapted to be removably engaged by a settable compound material injection device and a closed end inside said in-ear device adapted to receive said settable compound material allowing for said in-ear device to properly assume said ear canal of said individual, said method further comprises, after steps f) and i) respectively, the steps of:

f1) starting a slow injection of said compound material into said expandable in-ear device via said injection channel;

i1) repeating steps f) through i) to continuously monitor said calculated value of said sound level while simultaneously keeping on injecting said compound material;

i2) stopping said injection upon obtaining a calculated value of a sound pressure level difference of said in-ear device achieving first occurring of being either substantially equal to a predetermined sound pressure level difference or a substantially time stable sound level difference conditions.

Preferably, either said predetermined sound pressure level difference or said time stable sound level difference being determined over a pre-selected frequency range, said method further comprises, after step c), the step of:

c1) performing selection of said pre-selected frequency range for obtaining a corresponding calculated value of a sound pressure level difference.

Preferably, the computer unit including a display member, said method further comprises, between steps i) and i1), the step of:

i') displaying said calculated value of said sound level difference provided by said in-ear device on said display member.

Preferably, the method further comprises, after step l), the step of:

l1) waiting for said settable compound material to properly set before performing any following step.

Alternatively, the in-ear device has a second sound bore with an environment opening and an ear opening outside and inside said ear canal respectively, said environment opening of said second sound bore being adapted to be removably engaged by a second remote device, said method further comprises, after step a), the step of:

a1) engaging said second remote device being either an amplifier device or a filter device adapted for a preselected frequency window to said environment opening of said second sound bore.

Alternatively, steps a) to i) are simultaneously performed for a second in-ear device inserted into a second ear canal of said individual and using a corresponding second sound measurement device adapted to engage an environment opening of a sound bore of said second in-ear device.

Preferably, the computer unit containing pre-determined correction factors and a transfer coefficient, said method further comprises, after step i), the step of:

i') estimating an insertion loss value provided by said in-ear device from said calculated value of said sound level difference and said pre-determined correction factors and transfer coefficient.

BRIEF DESCRIPTION OF THE DRAWINGS

In the annexed drawings, like reference characters indicate like elements throughout.

DETAILED DESCRIPTION OF THE PREFERRED EMBODIMENTS

With reference to the annexed drawings the preferred embodiments of the present invention will be herein described for indicative purposes and by no means as of limitation.

Figure 1:
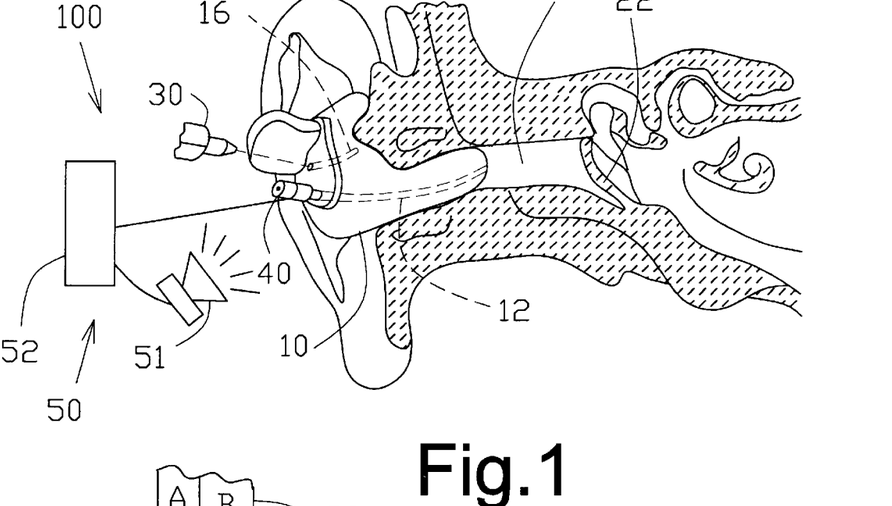
FIG. 1 shows an embodiment of an apparatus for determining in situ the acoustic seal provided by an in-ear device according to the present invention fitted into an ear canal of an individual.

Referring to FIG. 1, there is shown an embodiment 100 of an apparatus for determining in situ the acoustic seal, preferably leading to an attenuation or an amplification of the sound level, provided by an in-ear device 10, preferably a semi-custom-molded expandable earplug, inserted into an ear canal 20 of an individual.

Figure 2:
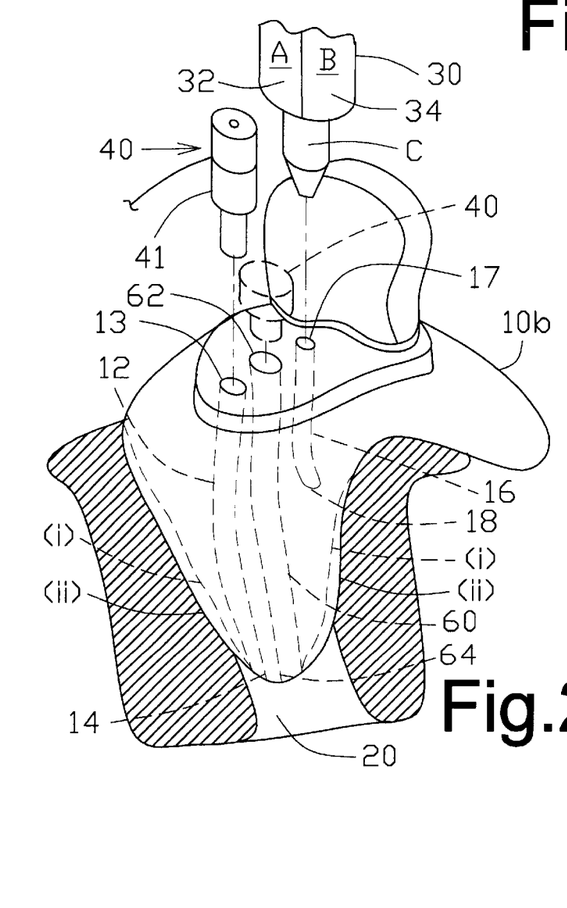
FIG. 2 is a perspective view of an expandable in-ear device used with the embodiment of FIG. 1 showing its shape before (i) and after (ii) expansion.

As it is shown in FIG. 2, the in-ear device 10 has a sound bore 12 with an environment opening 13 and an ear opening 14 outside and inside the ear canal 20 respectively. The environment opening 13 is adapted to be removably engaged by a remote device 40 such as a sound measurement device, a filter device, an hearing aid (or amplifier) device, a plug device and the like.

Figure 3:
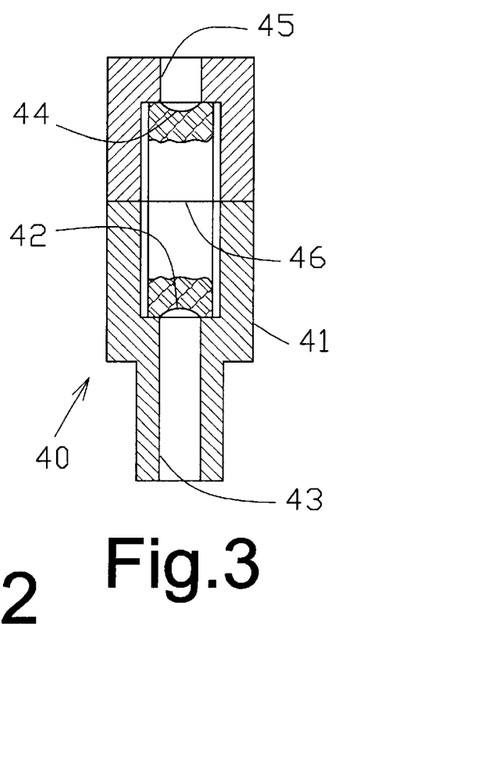
FIG. 3 is a section view of a sound measurement device of the embodiment of FIG. 1.

The apparatus 100 comprises a sound measurement device 41 as a remote device 40 (see FIG. 3) that has a probe microphone 42 and a reference microphone 44 connected to a data processing unit 50 and isolated from each other by isolation barrier 46 located between the probe 42 and reference 44 microphones for fully canceling any mutual influence. Microphones 42, 44 are typical microphones known in the industry such as EA-1954 or FG-3329 types from Knowles Electronics, Inc. Obviously, both microphones 42, 44 are pre-calibrated with respect to their position relative to their respective opening 43, 45 of the sound measurement device 41. The barrier 46 is preferably made out of potting compound or epoxy like material being a sound insulating material securing each microphone 42, 44 in place.

Figure 4:
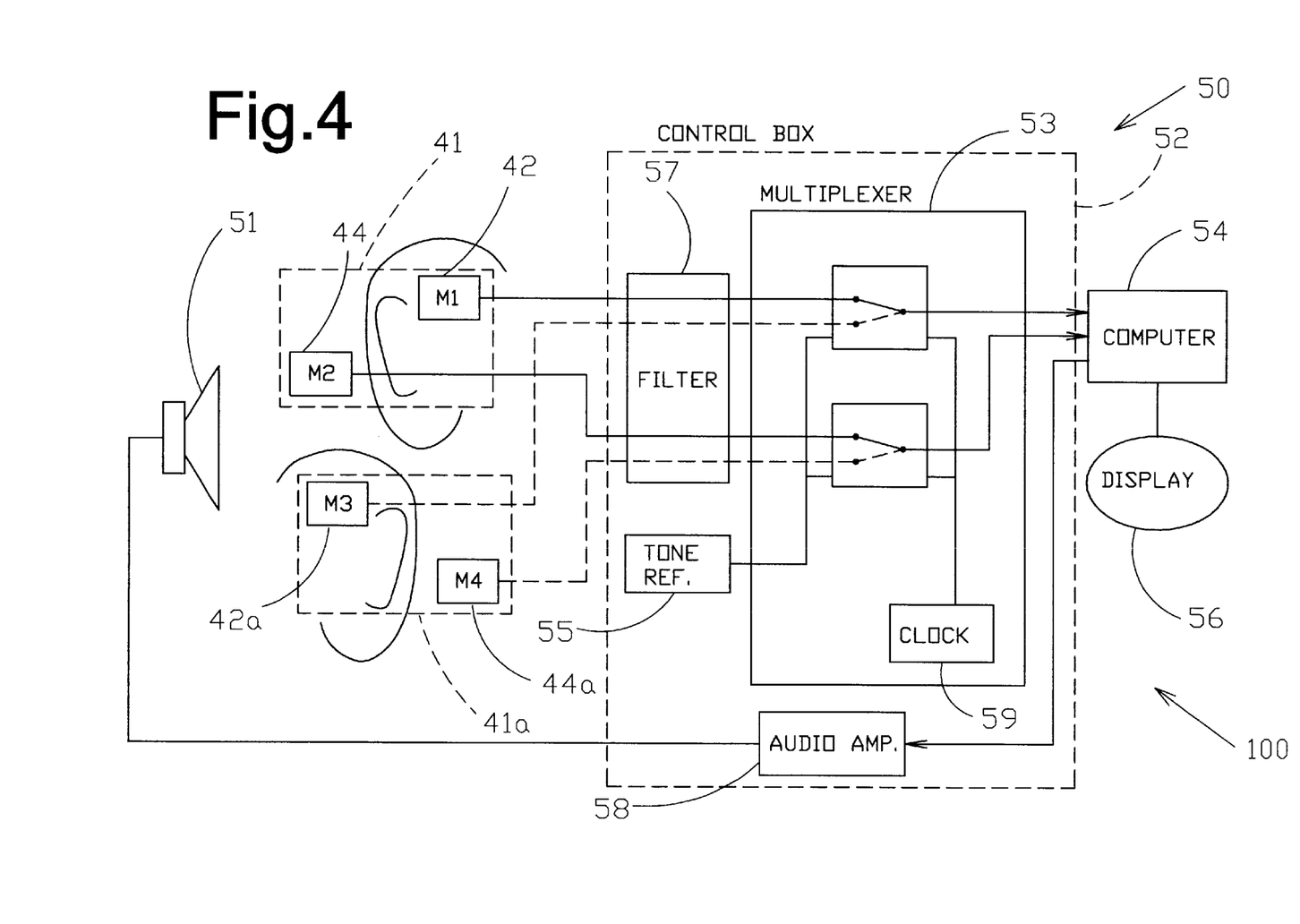
FIG. 4 shows a block diagram of the method of using the embodiment of FIG. 1.

Referring to FIG. 4 the data processing unit 50 has a control box 52 and a reference sound source or speaker 51, both connected to a computer unit 54. The probe 42 and the reference 44 microphones are adapted for measuring a sound pressure level inside the ear canal 20 of an individual and a sound pressure level from the environment in close proximity of the in-ear device 10 respectively (see FIGS. 1 and 5). The sound pressure levels corresponding to a known noise pressure signal created by the reference sound source 51 at an inlet to the individual's ear in a close proximity of the in-ear device 10 and inside the individual's ear canal 20, in proximity to the tympanic membrane 22 next to the ear drum. The sound pressure levels correspond to a known noise source signal, preferably of wide band ranging from twenty hertz (20 Hz) to twenty thousand hertz (20000 Hz) for enhanced measurements, coming from the computer unit 54 via an audio amplifier 58 of the control box 52 and speaker 51. The control box 52 is preferably an electronic controller adapted for gathering the sound pressure levels read by both microphones 42, 44 before transmitting them to the computer unit 54 to be recorded and processed by the same. Although the use of a standard micro-computer or a "laptop" computer is preferred, the computer unit 54 could be any other electronic system such as a dedicated system or larger computers.

The data processing unit 50 is adapted for recording and processing the sound pressure levels read by both probe 42 and reference 44 microphones corresponding to the known noise pressure signal to provide a corresponding calculated value of a sound level difference provided by the in-ear device 10. The computer unit 54 preferably includes a display member 56 for displaying the sound level difference calculated value provided by the in-ear device 10, being either an attenuation or an amplification depending on the type of in-ear device 10.

Optionally, the apparatus 100 further comprises a second measurement device 41a adapted to engage an environment opening 13 of a sound bore 12 of a second in-ear device 10 inserted into a second ear canal 20 of the individual. The second measurement device 41a is also connected to the control box 52 of the data processing unit 50 for the same to simultaneously provide a corresponding calculated second value of a second sound level difference provided by that second in-ear device 10. Accordingly, the display member 56 displays the sound level difference calculated values provided by respective in-ear devices 10.

Consequently, the control box 52 is also adapted for properly filtering the sound pressure levels read by the probe 42, 42a and reference 44, 44a microphones of both in-ear devices 10 using a filter circuit 57 and has a multiplexer circuit 53 for sequentially sending the filtered measured sound pressure levels of the microphones 42, 42a, 44, 44a of both sound measurement devices 41, 41a connected to both in-ear devices 10 to the computer unit 54 using an internal clock and tone reference trigger signal provided by a tone reference circuit 55, as shown in FIG. 4.

Preferably, the in-ear device 10b is expandable, from a first original shape (i) to a second final shape (ii) as shown in FIG. 2, and further has an injection channel 16 with an opened end 17 outside the ear canal 20 and a closed end 18 inside the in-ear device 10b adapted to receive a settable compound material (C) allowing for the in-ear device 10b to properly assume the ear canal 20 of the individual. Preferably, the compound material C, once set, has a hardness value between five (5) and forty (40) shore-A.

Consequently, the apparatus 100 is adapted for continuously monitoring the calculated value of the sound level difference while an operator is simultaneously slowly injecting the compound material C into the filling canal 16 of the expandable in-ear device 10b. The settable compound material C is preferably injected using a syringe 30 having two adjacent barrels 32, 34, each containing one of its two constituents A, B that are mixed during the injection (A+B= C). The data processing unit 50 is adapted for advising to stop injecting the compound material C into the expandable in-ear device 10b upon obtaining a calculated value of a sound pressure level difference of the in-ear device that achieves a first occurring of being either substantially equal to a predetermined sound pressure level difference or a substantially time stable sound level difference conditions. These conditions may be applicable to any frequency range selected by the operator before starting the injection. Obviously, the display member 56 continuously displays the sound pressure level difference calculated value provided by the in-ear device 10b in real time.

Optionally, the in-ear device 10 has a second sound bore 60 with an environment opening 62 and an ear opening 64 outside and inside the ear canal 20 respectively. The environment opening 62 is adapted to be removably engaged by a second remote device 40. That second remote device 40 is preferably either an amplifier device or filter device adapted for a pre-selected frequency window, or the like. The second remote device 40 does engage the environment opening 62 of the second sound bore 60 during the measurement of the sound pressure levels by the probe 42 and reference 44 microphones. When the second remote device 40 is an amplifier device, the measured sound pressure levels will show the amplification value of the signal and could serve to determine the absence of signal feedback because of a good acoustic seal between the in-ear device 10 and the individual's ear canal 20. In the case of a filter device or a plug, the measured sound pressure levels will show the attenuation value of the signal because of a good acoustic seal between the in-ear device 10 and the individual's ear canal 20. A plug 41 is preferably used to acousticly and physically close off the injection opening 62 during the injection, or occlusion, of the in-ear device 10 while the environment opening 13 is used for measurement.

Obviously, the data processing of any of the above sound pressure level measurements could provide a difference calculated value for any pre-selectable frequency range (any single frequency level included) that is either an average value or a frequency dependent variation over the selected range (such as discrete values for each octave over the frequency range).

The present invention also refers to a method for determining in-situ the acoustic seal provided by an in-ear device 10 inserted into an ear canal 20 of an individual. The in-ear device 10 has sound bore 12 with an environment opening 13 and an ear opening 14 outside and inside the ear canal 20 respectively. The environment opening 13 is adapted to be removably engaged by a remote device 40 such as a sound measurement device 41, a filter device, an hearing aid device, a plug device and the like.

The method preferably comprises the steps of:
a) providing the sound pressure measurement device 41 having a probe microphone 42 and a reference microphone 44 isolated from each other and a data processing unit 50 having a control box 52 and a speaker 51, both connected to a computer unit 54,
b) turning on the data processing unit 50;
b') performing calibration of the data processing unit 50 to check proper connection of the control box 52 to the computer unit 54;
c) connecting the measurement device 41 to the data processing unit 50;
d) testing connection of the measurement device 41 to the data processing unit 50 by measuring a known noise pressure signal from the speaker 51 with the probe 42 and reference 44 microphones;
e) engaging the measurement device 41 into the environment opening 13 of the sound bore 12, the probe 42 and reference 44 microphones for measuring a sound pressure level inside the ear canal 20 of the individual and a sound pressure level from the environment in close proximity of the in-ear device 10 respectively;
f) sending a known noise pressure signal from the speaker 51;
g) recording sound pressure levels read by both probe 42 and reference 44 microphones corresponding to the known noise pressure source signal 51;
h) processing the measured sound pressure levels;
i) obtaining a calculated value of a sound level difference provided by the in-ear device 10;
j) turning off the data processing unit 50;
k) disconnecting the measurement device 41 from the data processing unit 50;
l) disengaging the measurement device 41 from the in-ear device 10;
m) connecting another remote device 40 to the environment opening 13 of the sound bore 12 of the in-ear device 10.

Additionally, steps a) to i) of the method could be simultaneously performed for a second in-ear device 10 inserted into a second ear canal 20 of the individual and using a corresponding second sound measurement device 41a adapted to engage an environment opening 13 of a sound bore 12 of the second in-ear device 10.

Preferably, the in-ear device 10b is expandable and further has an injection channel 16 with an opened end 17 outside the ear canal 20 adapted to be removably engaged by a settable compound material injection device such as a syringe 30, and a closed end 18 inside the in-ear device adapted to receive a settable compound material (C) allowing for the in-ear device 10b to properly assume the ear canal 20 of the individual. The method further comprises, after steps f), i) and l) respectively, the steps of:
f1) starting a slow injection of the compound material C into the expandable in-ear 10b device via the injection channel 16;
i1) repeating steps f) through i) to continuously monitor the calculated value of the sound level while simultaneously keeping on injecting the compound material C;
i2) stopping the injection upon obtaining a calculated value of a sound pressure level difference of the in-ear device 10b achieving first occurring of being either substantially equal to a predetermined sound pressure level difference or a substantially time stable sound level difference conditions;
l1) waiting for the settable compound material C to properly set before removing the expandable in-ear device 10b from said ear canal 20 or performing any following step.

Optionally, either the predetermined sound pressure level difference or the time stable sound level difference is determined over a pre-selected frequency range. The method then further comprises, after step c), the step of:
c1) performing selection of the pre-selected frequency range for obtaining a corresponding calculated value of a sound pressure level difference.

Also, the computer unit 54 includes a display member 56, and the method further comprising, between steps i) and i1), the step of:
i') displaying the calculated value of the sound level difference provided by the in-ear device 10a on the display member 56.

Obviously, the above method could be performed along with an in-ear device 10 having a second sound bore 60 with an environment opening 62 and an ear opening 64 outside and inside the ear canal 20 respectively. The environment opening 62 is adapted to be removably engaged by a second remote device 40. That second remote device 40 is preferably either an amplifier device or filter device adapted for a pre-selected frequency window, or the like during measurement; or a plug during injection of the in-ear device 10.

Figure 5A:
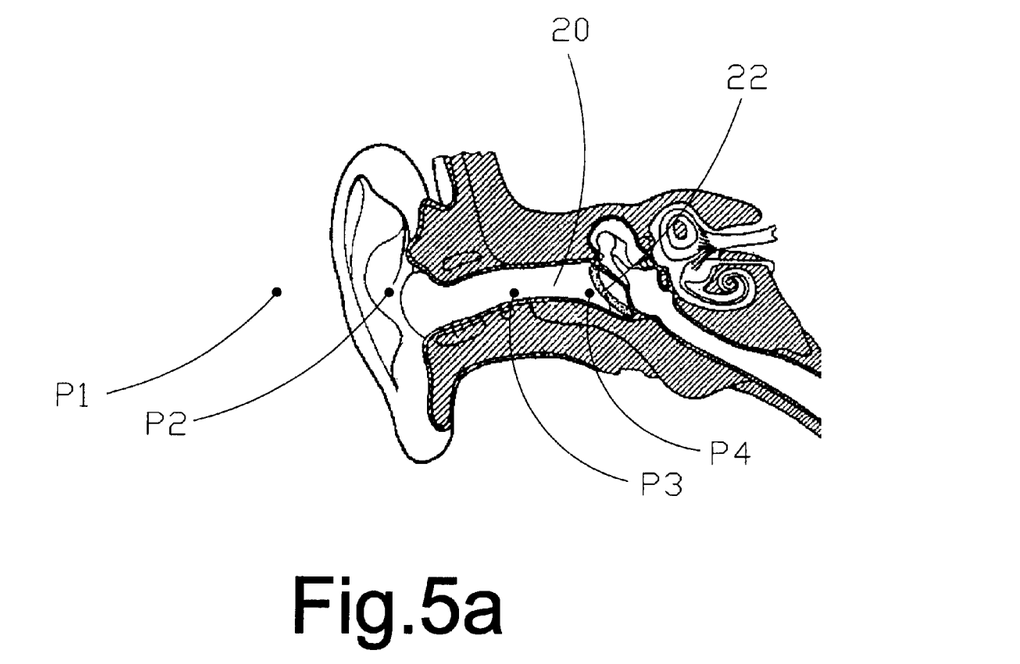
FIGS. 5a and 5b show pictorial representations of the different locations for sound pressure level measurement inside an individual's ear canal without and with an in-ear device respectively, in order to determine an insertion loss estimation from the acoustic seal provided by the in-ear device and determined by the embodiment of FIG. 1.
Figure 5B:
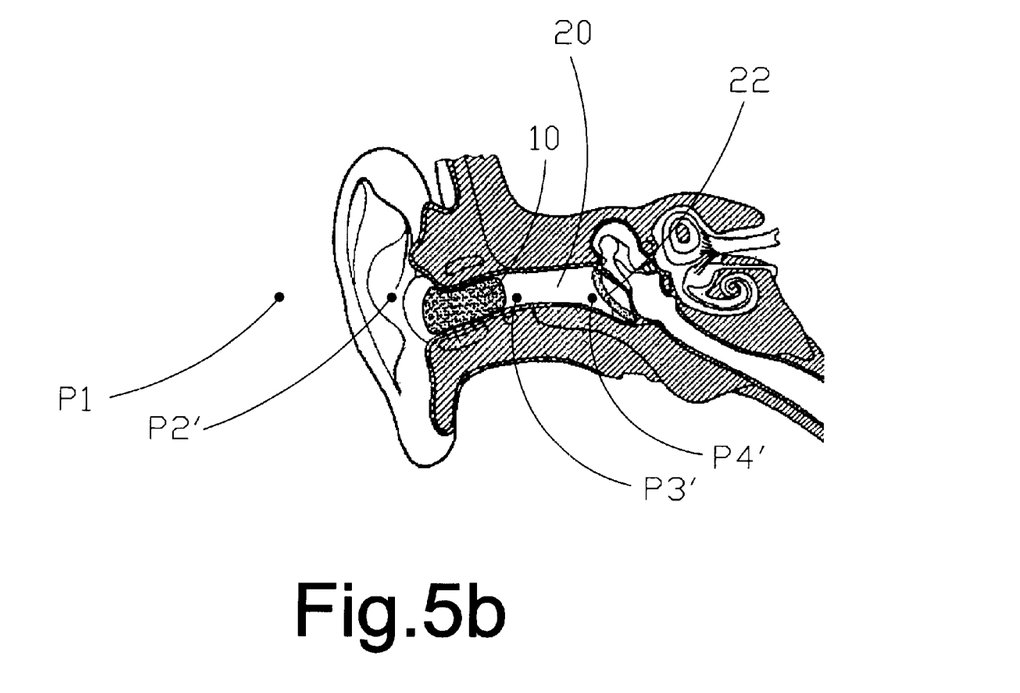

Referring to FIGS. 5a and 5b, there is shown pictorial representations of the different locations for sound pressure level measurement inside and outside an individual's ear canal 20 without and with an in-ear device 10 respectively. All standards, such as ANSI, ISO, CSA and the like, require an insertion loss (IL) subjective estimation, generally expressed in dB (decibels), of the acoustic seal provided by the in-ear device based on a ratio of Real Ear Attenuation Threshold (REAT) values determined at the tympanic membrane, or eardrum, by the individual himself (thereby subjective), with and without the in-ear device 10, i.e. IL=20 $\log_{10}(P_4/P_4')$ in logarithmic notation.

Using the apparatus 100, the IL can be objectively determined by IL=NR+TFOE where the noise ratio (NR) equals to 20 $\log_{10}(P_1/P_4')$ is determined by the sound pressure levels measured at the outer ($P_2'$) and inner ($P_3'$) extremities of the in-ear device and reported to $P_1$ and $P_4'$ respectively using corresponding pre-determined correction factors contained within the computer unit 54, and the Transfer Function of the Outer Ear (TFOE) being also a transfer coefficient corresponding to 20 $\log_{10}(P_4/P_1)$ contained within the computer unit 54. The transfer coefficient of the TFOE is preferably a mean value of different and already measured values of different sizes and shapes of ears available from many widely known publications by anyone familiar with the art. Since the variation of these different known TFOE values is relatively low below 1000 Hz, the determination of a mean TFOE value is suitable for the purpose of an objective estimation of IL in the present case.

Accordingly, the computer unit 54 containing the pre-determined correction factors and the transfer coefficient allows for the apparatus 100 to determine an estimated insertion loss IL value of the acoustic seal provided by the in-ear device 10 from the calculated value of the sound level difference leading to the NR using the pre-determined correction factors and the predetermined transfer coefficient.

Finally, from this IL value, it is possible to extract other different standard parameters or indicators such as the noise reduction rating (NRR), the class, the single number rating (SNR) or the like, depending on the applicable standard.

Although embodiments of the invention have been illustrated in the accompanying drawings and described in the foregoing detailed description, it will be understood that the invention is not limited to the embodiments disclosed, but is capable of numerous rearrangements, modifications, and substitutions without departing from the scope of the invention.

I claim:

1. An apparatus for determining in situ an acoustic seal provided by an in-ear device inserted into an ear canal of an individual, said in-ear device having a sound bore with an environment opening and an ear opening outside and inside said ear canal respectively, said environment opening being adapted to be removably engaged by a remote device such as a sound measurement device, a filter device, an amplifier device, a plug device and the like, said apparatus comprising a sound measurement device being said remote device and having a probe microphone and reference microphone isolated from each other and connected to a data processing unit having a control box and a reference sound source, both connected to a computer unit, said probe and reference microphones being adapted for measuring a sound pressure level inside said ear canal of said individual and a sound pressure level from said environment in close proximity of said in-ear device respectively, said sound pressure levels corresponding to a known noise signal created by said reference sound source at an inlet to the individual's ear in a close proximity of said in-ear device, said data processing unit being adapted for recording and processing said sound pressure levels read by both said probe and reference microphones corresponding to said known noise signal to provide a corresponding calculated value of a sound level difference provided by said in-ear device.

2. An apparatus as defined in claim 1, wherein said in-ear device being expandable and further having an injection channel with an opened end outside said ear canal and a closed end inside said in-ear device adapted to receive a settable compound material allowing for said in-ear device to properly assume said ear canal of said individual, said apparatus being adapted for continuously monitoring said calculated value of said sound level difference while said compound material being simultaneously slowly injected into said expandable in-ear device via said injection channel, said data processing unit being adapted for advising to stop injecting said compound material into said expandable in-ear device upon obtaining a calculated value of a sound pressure level difference of said in-ear device achieving first occurring of being either substantially equal to a predetermined sound pressure level difference or a substantially time stable sound level difference conditions.

3. An apparatus as defined in claim 2, wherein either said predetermined sound pressure level difference or said time stable sound level difference being determined over a pre-selected frequency range.

4. An apparatus as defined in claim 1, further comprising a second measurement device adapted to engage an environment opening of a sound bore of a second in-ear device inserted into a second ear canal of said individual, said second measurement device being simultaneously connected to said control box of said data processing unit for the same to simultaneously provide a second corresponding calculated value of a sound level difference provided by said second in-ear device.

5. An apparatus as defined in claim 1, wherein said computer unit including a display member for displaying said calculated value of said sound level difference provided by said in-ear device.

6. An apparatus as defined in claim 3, wherein said computer unit including a display member for displaying said calculated value of said sound level difference provided by respective of said in-ear devices.

7. An apparatus as defined in claim 4, wherein said computer unit includes a display member for continuously displaying said calculated value of said sound level difference provided by said in-ear device.

8. An apparatus as defined in claim 5, wherein said control box being adapted for filtering and sequentially sending said sound pressure levels read by said probe and reference microphones of said in-ear device to said computer unit.

9. An apparatus as defined in claim 6, wherein said control box being adapted for filtering said sound pressure levels read by said probe and reference microphones of both of said in-ear devices and having a multiplexer for sequentially sending the same to said computer unit.

10. An apparatus as defined in claim 1, wherein said in-ear device having a second sound bore with an environment opening and an ear opening outside and inside said ear canal respectively, said environment opening of said second sound bore being adapted to be removably engaged by a second remote device, said second remote device being either an amplifier device or filter device adapted for a pre-selected frequency window, said second remote device engaging said environment opening of said second sound bore during measuring said sound pressure levels by said probe and reference microphones.

11. An apparatus as defined in claim 1, wherein said computer unit containing pre-determined correction factors and a transfer coefficient, said apparatus determining an estimated insertion loss value provided by said in-ear device from said calculated value of said sound level difference and said predetermined correction factors and transfer coefficient.

12. A method for determining in-situ the acoustic seal provided by an in-ear device inserted into an ear canal of an individual, said in-ear device having a sound bore with an environment opening and an ear opening outside and inside said ear canal respectively, said environment opening being adapted to be removably engaged by a remote device such as a sound measurement device, a filter device, an amplifier device, a plug device and the like, said method comprising the steps of:

a) providing said sound measurement device having a probe microphone and a reference microphone isolated from each other and a data processing unit having a control box and a reference sound source, both connected to a computer unit, b) turning on said data processing unit;

c) connecting said measurement device to said data processing unit;

d) testing connection of said measurement device to said data processing unit by measuring a known noise signal from said reference sound source with said probe and reference microphones;

e) engaging said measurement device into said environment opening of said sound bore, said probe and reference microphones for measuring a sound pressure level inside said ear canal of said individual and a sound pressure level from said environment in close proximity of said in-ear device respectively;

f) sending a known noise signal from said reference sound source;

g) recording sound pressure levels read by both said probe and reference microphones corresponding to said known noise source signal;

h) processing said measured sound pressure levels;

i) obtaining a calculated value of a sound level difference provided by said in-ear device;

j) turning off said data processing unit;

k) disconnecting said measurement device from said data processing unit; and l) disengaging said measurement device from said in-ear device.

13. A method as defined in claim 12, further comprising, after step b), the step of:

b1) performing calibration of said data processing unit to check proper connection of said control box to said computer unit.

14. A method as defined in claim 13, wherein said in-ear device being expandable and further having an injection channel with an opened end outside said ear canal adapted to be removably engaged by a settable compound material injection device and a closed end inside said in-ear device adapted to receive said settable compound material allowing for said in-ear device to properly assume said ear canal of said individual, said method further comprising, after steps f) and i) respectively, the steps of:

f1) starting a slow injection of said compound material into said expandable in-ear device via said injection channel;

i1) repeating steps f) through i) to continuously monitor said calculated value of said sound level while simultaneously keeping on injecting said compound material;

i2) stopping said injection upon obtaining a calculated value of a sound pressure level difference of said in-ear device achieving first occurring of being either substantially equal to a predetermined sound pressure level difference or a substantially time stable sound level difference conditions.

15. A method as defined in claim 14, wherein either said predetermined sound pressure level difference or said time stable sound level difference being determined over a pre-selected frequency range, said method further comprising, after step c), the step of:

c1) performing selection of said pre-selected frequency range for obtaining a corresponding calculated value of a sound pressure level difference.

16. A method as defined in claim 15, said computer unit including a display member, said method further comprising, between steps i) and i1), the step of:

i') displaying said calculated value of said sound level difference provided by said in-ear device on said display member.

17. A method as defined in claim 16, further comprising, after step l), the step of:

l1) waiting for said settable compound material to properly set before performing any following step.

18. A method as defined in claim 12, wherein said in-ear device having a second sound bore with an environment opening and an ear opening outside and inside said ear canal respectively, said environment opening of said second sound bore being adapted to be removably engaged by a second remote device, said method further comprising, after step a), the step of:

a1) engaging said second remote device being either an amplifier device or a filter device adapted for a pre-selected frequency window to said environment opening of said second sound bore.

19. A method as defined in claim 12, wherein steps a) to i) are simultaneously performed for a second in-ear device inserted into a second ear canal of said individual and using a corresponding second sound measurement device adapted to engage an environment opening of a sound bore of said second in-ear device.

20. A method as defined in claim 12, wherein said computer unit containing pre-determined correction factors and a transfer coefficient, said method further comprising, after step i), the step of:

i') estimating an insertion loss value provided by said in-ear device from said calculated value of said sound level difference and said pre-determined correction factors and transfer coefficient.

* * * * *